United States Patent [19]

Lane

[11] Patent Number: 4,708,146

[45] Date of Patent: Nov. 24, 1987

[54] APPARATUS AND METHOD FOR IMPEDANCE PNEUMOGRAPHY

[75] Inventor: Philip S. Lane, Redmond, Wash.

[73] Assignee: SpaceLabs, Inc., Bothell, Wash.

[21] Appl. No.: 893,834

[22] Filed: Aug. 6, 1986

[51] Int. Cl.$^4$ .............................................. A61B 5/08
[52] U.S. Cl. .................................. 128/723; 324/65 R
[58] Field of Search ...................... 128/723, 693, 734; 324/65 R

[56] References Cited

U.S. PATENT DOCUMENTS 3,532,087 10/1970 Horn et al. ........................... 128/723
3,802,419 4/1974 Yates .................................... 128/723
3,882,851 5/1975 Sigworth ......................... 128/723 X Primary Examiner—Lee S. Cohen
Attorney, Agent, or Firm—Seed and Berry

[57] ABSTRACT

An apparatus and method for monitoring the expansion and contraction of the thoracic cavity during respiration is disclosed. A constant current carrier is passed through the thorax of a patient using a pair of ECG leads. The resulting amplitude modulated voltage signal is synchronously detected using a reference signal which is phase-locked to the amplitude modulated voltage signal. A phase locked loop (PLL) having a tri-state phase comparator and a voltage controlled oscillator (VCO) is used to generate the reference signal. A dead zone compensation circuit is coupled to the VCO to provide a trickle current that causes the tri-state phase comparator to be biased out of its null state.

11 Claims, 6 Drawing Figures

APPARATUS AND METHOD FOR IMPEDANCE PNEUMOGRAPHY

BACKGROUND OF THE INVENTION

The present invention relates to impedance pneumography which is a technique for monitoring the expansion and contraction of the thoracic cavity during respiration.

Typically, a low level, constant current carrier is passed through the thorax via two ECG electrodes, for example, the Right Arm and Left Arm ECG electrodes. As respiration of the patient occurs, the patient's baseline impedance will vary slightly causing an amplitude-modulated voltage to be developed which is then synchronously detected. In the prior art, the reference used for the synchronous detector is the same clock used to develop the constant current drive.

A synchronous demodulator detects both amplitude and also phase information. If the phase of the input signal differs from that of the reference signal by 90 degrees the filtered output will decrease to zero. In a constant current pneumography system, the voltage developed across the patient (the incoming signal) may not be in phase with the carrier current and its associated drive signal (the reference input). This phase differential depends on the phase angle of the load impedance (the patient) which in practice can vary arbitrarily. When the incoming carrier voltage from the patient is synchronously demodulated using the original carrier drive signal as a reference, this variable phase shift is detected along with the amplitude modulation creating undesirable noise in the output. In such a system the displayed respiration trace can be easily perturbed by moving the patient cable or even just walking next to the patient. This type of noise is undesirable in general and can upset the inspiration detector.

SUMMARY OF THE INVENTION

An apparatus for monitoring the respiration of a patient is provided. A constant current carrier signal is generated and coupled to the thorax of a patient preferably through a pair of ECG leads. The resultant amplitude modulated signal is synchronously detected using a reference frequency which is phase-locked to the same incoming signal.

In the preferred embodiment a phase locked loop (PLL) is used to generate the reference frequency. The PLL includes a tri-state phase comparator and a voltage controlled oscillator (VCO). The PLL circuit further comprises a dead zone compensation circuit in the phase detector output to provide a trickle current to bias the tri-state phase comparator out of its null state into a predetermined one of its remaining two states.

DETAILED DESCRIPTION OF THE DRAWINGS

Figure 1:
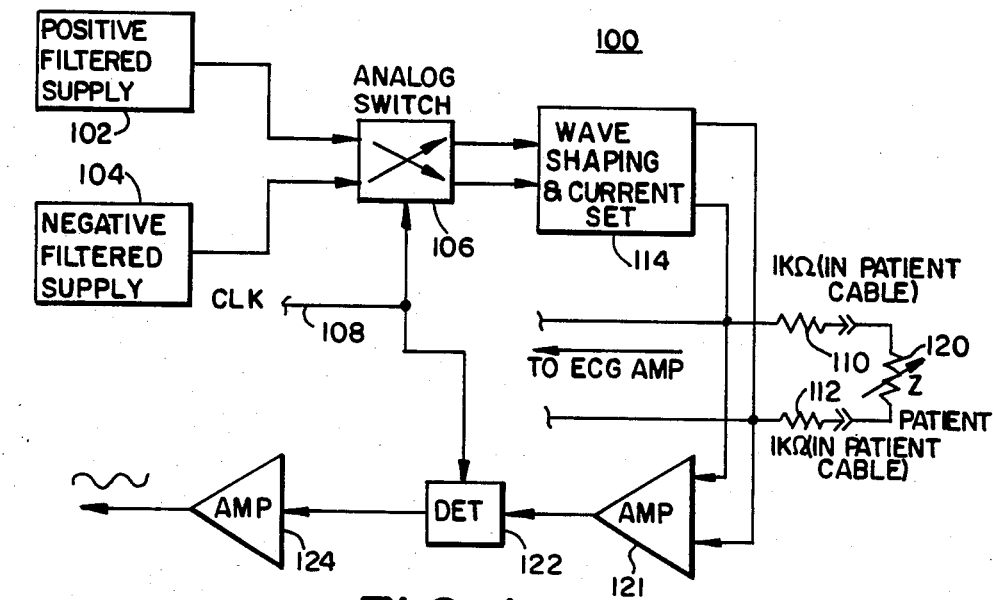
FIG. 1 is a block diagram of a prior art impedance neumography system.

Referring now to FIG. 1, in the prior art, the impedance pneumography system designated generally 100 comprises positive and negative filtered supplies 102 and 104, respectively, which generate plus and minus five volt signals which are switched on and off alternately by the analog switch commutator 106 in response to a commutator drive signal 108 derived from a system clock.

The resultant complementary square waves are filtered and AC coupled to two ECG leads 110 and 112 by waveform circuit 114. The two leads are coupled to the patient represented by the variable impedance 120.

The circuit portion just described generates a low level, constant current carrier which is passed through the thorax of the patient via the Right Arm and Left Arm ECG electrodes. The carrier is typically in the 40 to 60 kHz range with amplitudes of 100 or 200 microamps peak to peak.

The baseline impedance of the patient 120 is about 1000 ohms and it will vary by about one ohm or less due to respiration. The amplitude modulated (AM) voltage developed across the patient 120 is amplified by the AC coupled differential carrier amplifier 121 whose output is fed to a full wave synchronous detector 122 which uses as a reference the commutator drive signal 108.

The detected signal from the full wave synchronous detector 122 contains a DC level corresponding to the relatively high shoulder-to-shoulder baseline impedance of the patient. In some prior art approaches this DC level is partially removed by substracting off a fraction of the original carrier drive reference voltage. Any noise caused by arbitrary fluctuation of the reference will be partially cancelled out. Depending on the implementation, this is sometimes accomplished within the synchronous detector which is an integrated circuit. Whether or not a subtraction scheme is used, the signal is eventually directed to a bandpass amplifier 124 to remove any residual DC, filter out carrier ripple and amplify the very small respiration signal.

Figure 2:
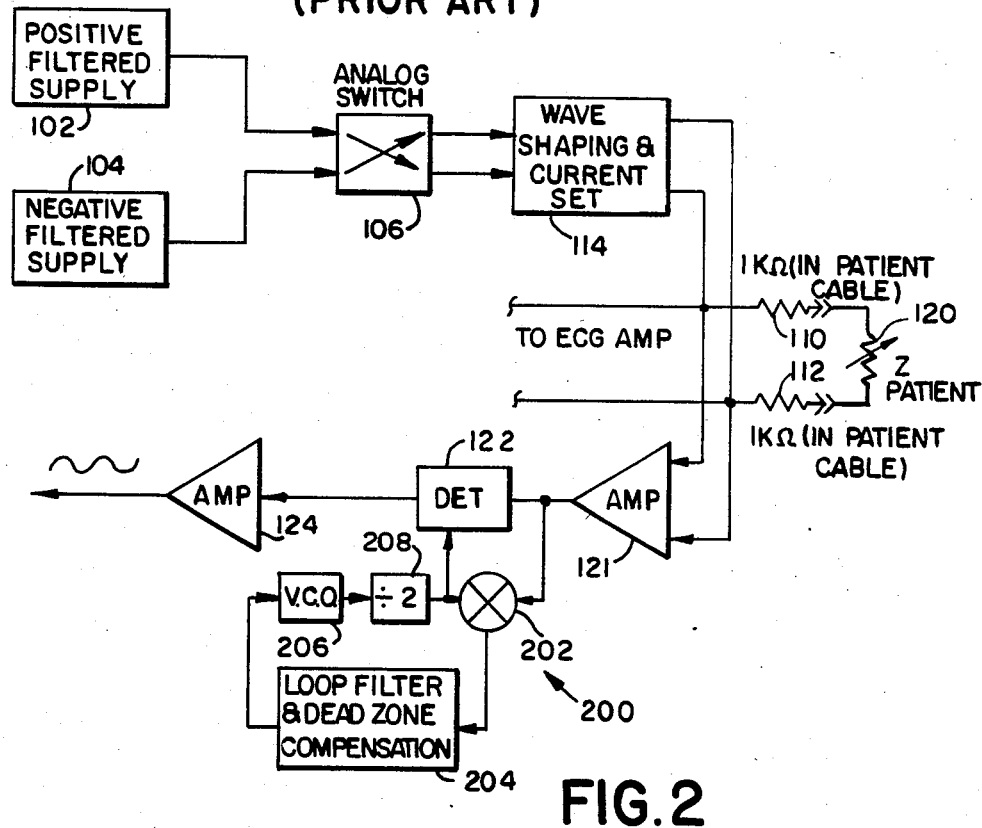
FIG. 2 is a block diagram of the pneumography system of the present invention.

In FIG. 2, a block diagram of the impedance pneumography system of the present invention is provided. Circuits generally the same in FIGS. 1 and 2 are numbered the same in both figures. The only difference is that the reference for the full wave synchronous detector 122 is not provided by the commutator drive 108 but by a phase lock loop PLL circuit designated generally 200 using a tri-state phase comparator 202. The AM signal output from amplifier 121 is provided to the detector circuit 122 and also as one input to the phase comparator 202. The output of the phase comparator after passing through a dead zone compensation circuit and loop filter 204 drives a voltage controlled oscillator 206 who's output frequency is twice that of the AM carrier. Hence, it is divided by two by circuit 208 before its output is provided as the reference for the detector 122 and as a feedback input to phase comparator 202. (With a tri-state phase comparator, the VCO runs in phase with the input signal, while with a conventional phase comparator, a phase lock loop will run with a 90 degree phase shift between the VCO and the input signal.) The output of the PLL 200 is used as the demodulator reference, and will always be phase-locked to the incoming carrier. As the phase of the respiration signal varies, the PLL-derived reference will also vary. Accordingly, any variation in phase between the constant-current reference drive and the voltage developed across the patient is ignored.

Figure 3:
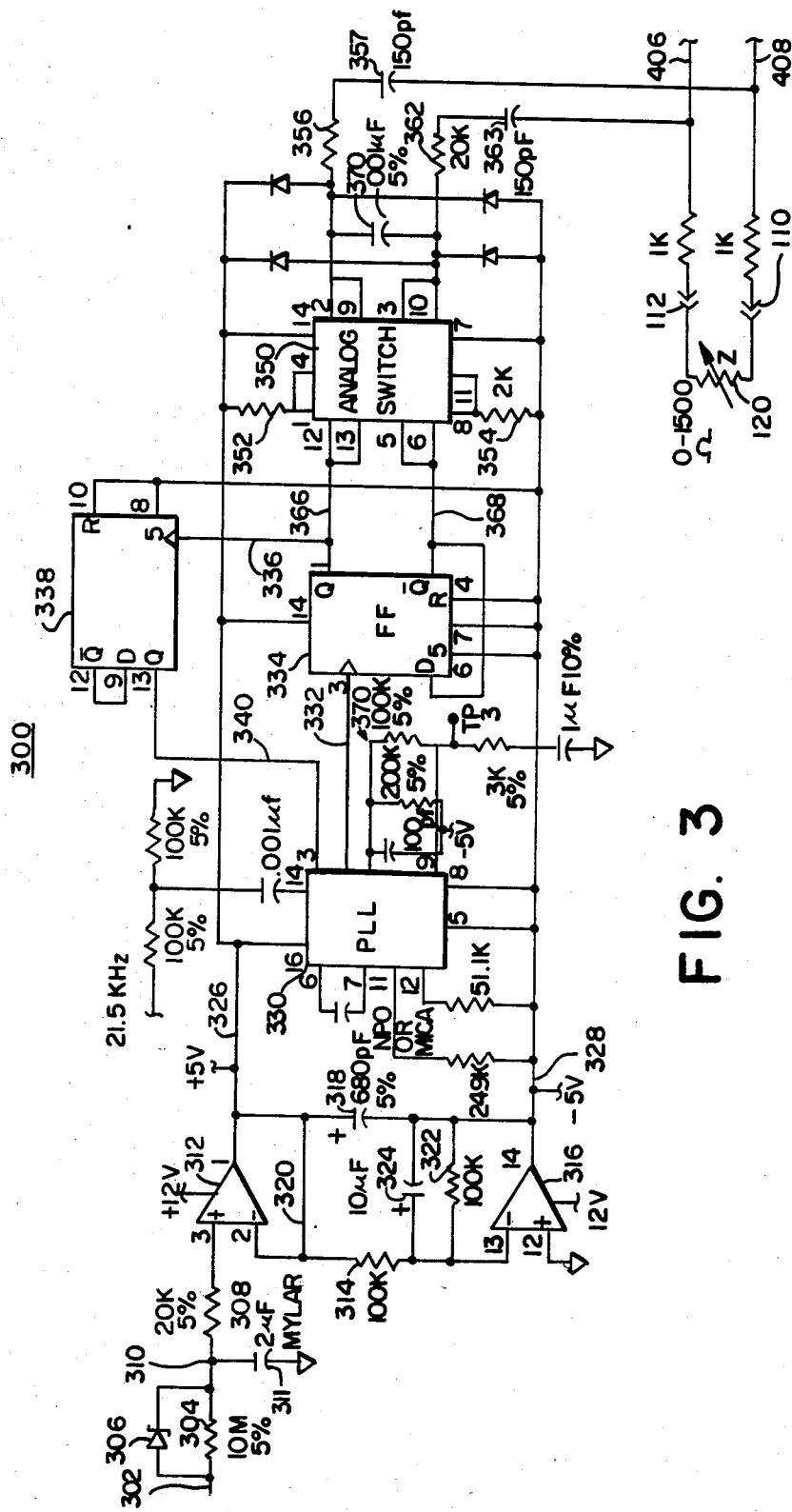
FIG. 3 is a more detailed circuit schematic of a first portion of the block diagram of FIG. 2.

Referring now to FIG. 3, a more detailed circuit showing the plus and minus 5 volt low noise power supplies and carrier generator portion designated generally 300 of the circuit is described. A crude 5 volt reference at 302 is low-pass filtered to 0.01 Hz by the resistor 304 and capacitor 311. Diode 306 is used to provide a fast charge-up when power is first applied. The output of the filter feeds resistor 308.

The other side of resistor 308 from junction 310 is coupled to the plus input terminal of buffer amplifier 312. Resistor 308 prevents excessive current flow into Op Amp 312 when power is removed. The output of amplifier 312 is coupled through resistor 314 to the negative input terminal of inverting amplifier 316. Their outputs are coupled together though capacitor 318 which provides low output impedance at high frequencies. The output of buffer amplifier 312 is coupled to its negative input directly via line 320 on one side of both resistor 314 and capacitor 318. The output of amplifier 316 is coupled through resistor 322 and parallel capacitor 324 to its negative input terminal on the other side of resistor 314 and capacitor 318. The positive input terminal of amplifier 316 is coupled to ground. The pair of buffer amplifiers 312 and 316 and the circuit just described coupling them together buffer and invert the reference input to amplifier 312 to provide a low noise, bipolar 5 volt rail, i.e., low noise plus and minus 5 volt signals on lines 326 and 328, respectively.

An RCA made model number CD4046B integrated circuit phase lock loop (PLL) 330, supplied with a 21.5 kHz, 10 volts peak to peak clock input at pin 14, comprises an internal voltage controlled oscillator which provides an 86 kHz output signal on line 332 coupled to the clock input of flip flop 334. The Q output of flip flop 334 at 43 kHz is coupled via line 336 to the clock input of flip flop 338. The Q output of flip flop 338 at 21.5 kHz is in turn coupled to pin 3 of PLL 330 via line 340 to complete the phase lock loop. (The essential purpose of this PLL is to multiply the 21.5 kHz clock frequency by two to provide a more suitable frequency for pneumography.)

The circuit 300 further comprises an RCA made model number CD4016B analog switch circuit 350. The plus 5 volt and minus 5 volt rail signals on lines 326 and 328, respectively, are coupled to the analog switch 350 via 2K ohm resistors 352 and 354 respectively. One output of switch 350 associated with resistor input 352 is disposed to be coupled via 20K ohm resistor 356 in series with capacitor 357 to the ECG electrode 110 coupled to the patient represented by the variable impedance 120, while a second output associated with resistor input 354 is disposed to be coupled via 20K ohm resistor 362 in series with capacitor 363 to the other ECG electrode 112. In addition the Q and $\overline{Q}$ outputs of flip flop 334 are coupled via leads 366 and 368 respectively to first and second switch control input terminals of the switch 350. The Q line 366 switches the +5 volt signal from line 326 through resistor 352 to the output through resistor 356 and capacitor 357 at a 43 kHz rate. Similarly, but 180° out of phase, the $\overline{Q}$ line 368 switches the minus 5 volt signal from line 328 through resistor 354 to the output through resistor 362 and capacitor 363 at a 43 kHz rate. A capacitor 370 coupled across the two outputs of switch 350 smoothes the square wave output of flip flop 334 so that a rough approximation sine wave is produced. Hence, the result obtained from circuit 300 is that a low level, constant current carrier is passed through the thorax of the patient (impedance 120) via two ECG electrodes 110 and 112, e.g., the Right Arm and Left Arm ECG electrodes. (Current is relatively constant as long as the patient impedance variation is low relative to 20K ohm resistors 356 and 362.)

The patient will exhibit a baseline impedance of about 1000 ohms at frequencies in the 40 to 60 kHz range. As respiration occurs, the impedance will vary by about one ohm or less.

Figure 4:
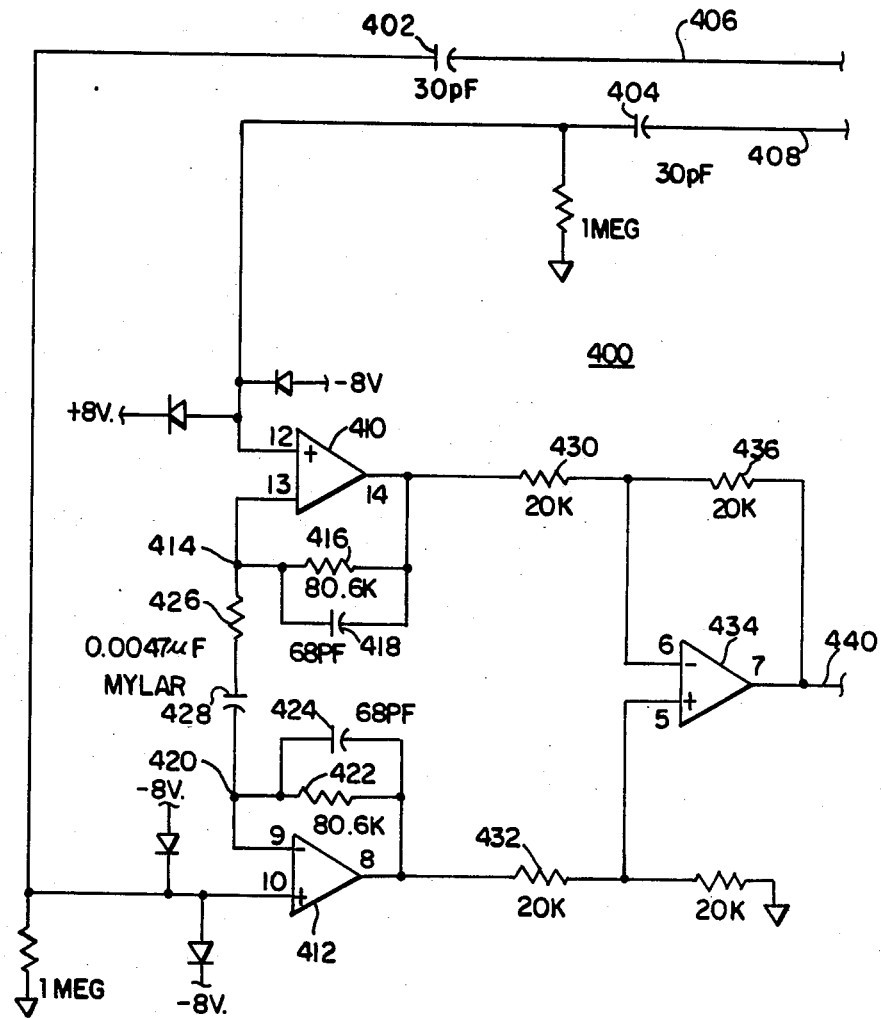
FIG. 4 is a more detailed circuit schematic of a second portion of the block diagram of FIG. 2.

Referring now to FIG. 4, a low noise differential amplifier designated generally 400 is AC coupled via capacitors 402 and 404, and associated leads 406 and 408, respectively, to the AM voltage developed across the patient. The AC coupled differential amplifier comprises operational amplifiers 410, 412, and 434. The output of amplifier 410 is coupled to its negative input terminal at junction 414 through resistor 416 and parallel capacitor 418 while the output of amplifier 412 is coupled at junction 420 through resistor 422 and parallel capacitor 424. Junction 414 and 420 are coupled via resistor 426 in series with capacitor 428.

The output of amplifiers 410 and 412 are coupled through resistors 430 and 432, respectively, to the negative and positive input terminals of amplifier 434. The output of amplifier 410 is also coupled through resistor 436 to the output of amplifier 434. The AC coupled differential amplifier of FIG. 4 serves as an amplifier of the carrier voltage developed across the patient producing a maximum output signal on lead 440 approximately six to eight volts peak-to-peak. The circuit of FIG. 4 provides an AC gain of about 10 while only a unity gain at DC.

Figure 5:
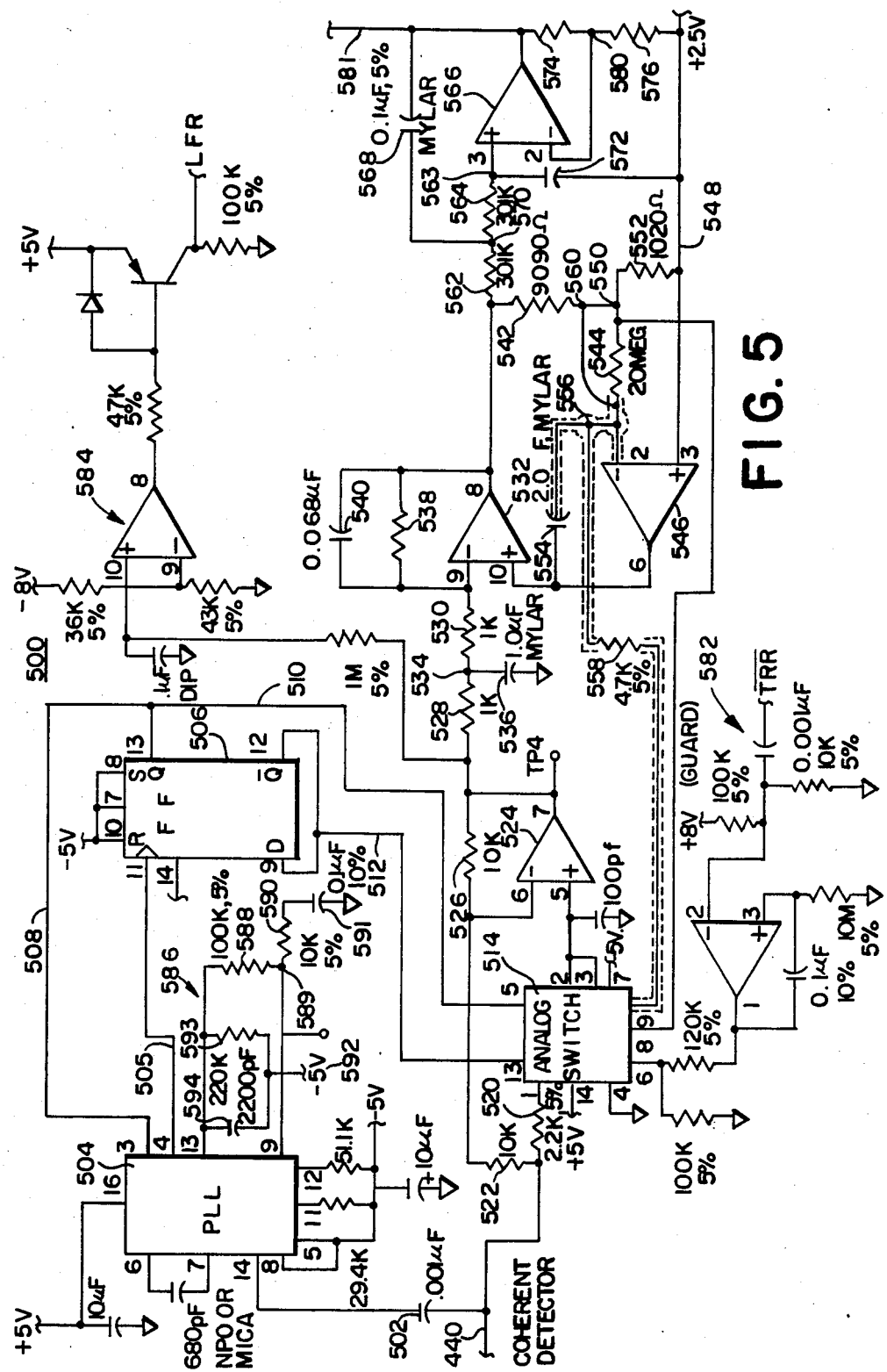
FIG. 5 is a more detailed circuit schematic of a third portion of the block diagram of FIG. 2.

Referring now to FIG. 5, the coherent detector, AC coupled amplifier and output low pass filter portions designated generally 500 of the circuit are described. The output of the amplifier of FIG. 4 at 43 kHz is provided via line 440 as a clock input via capacitor 502 to a PLL integrated circuit 504 identical to PLL integrated circuit 330. The PLL circuit 504 provides an 86 kHz clock via line 505 to the clock input of flip flop 506 whose Q output at 43 kHz is fed back via line 508 to the PLL circuit where the phase lock loop is closed.

Complementary square waves, phase locked to the incoming respiration signal on line 440, are provided from the Q and $\overline{Q}$ output of flip flop 506 on lines 510 and 512, respectively, as switch control signals to the analog switch 514 which is an RCA made model number CD4066B device.

The respiration signal from line 440 is coupled as an input to switch 514 via 2.2K ohm resistor 520 and via 10K ohm resistor 522 to the negative input terminal of a polarity-reversing unity gain amplifier 524. The output of the amplifier 524 is fed back via 10K ohm resistor 526 to its negative input terminal. The analog switch in combination with the amplifier 524 in response to the Q and $\overline{Q}$ outputs of flip flop 506 synchronously rectify the respiration signal.

The output of amplifier 524 is fully rectified varying from 0 to minus 3 or 4 volts and is coupled through 1K resistor 528 and 1K resistor 530 to the negative input of operational amplifier 532. The junction 534 between resistors 528 and 530 is coupled to ground by capacitor 536. The output of amplifier 532 is fed back to its negative input via resistor 538 and capacitor 540 in parallel with resistor 538. The output of amplifier 532 is also coupled through resistor 542 in series with resistor 544 to the negative input of amplifier 546 whose output is coupled to the positive input of terminal of amplifier 532. A 2.5 volt bias source is coupled via line 548 to the positive input terminal of amplifier 546. The junction 550 between resistors 542 and 544 is coupled to line 548 via resistor 552. The output of amplifier 546 is coupled to its negative input terminal via capacitor 554. Junction 556 between capacitor 554 and the negative input terminal of amplifier 546 is coupled via resistor 558 to the analog switch 514. The lines between resistor 544 and the amplifier 546, between capacitor 554 and the negative input terminal of amplifier 546 and between junction 556 and switch 514 are surrounded on the printed circuit board by guard traces to prevent any leakage from this high impedance circuitry. The guard run is coupled to a junction 560 between resistor 542 and junction 550 which provides a low impedance drive.

The resistor 528 and capacitor 536 smooth the rectified output of amplifier 524 to provide a DC voltage to the input of amplifier 532. The DC voltage will vary slowly with the respiration of the patient. The circuit described in connection with amplifier 532 and 546 provides an AC coupled amplifier which blocks the baseline DC due to the filtered rectified output of amplifier 524 but which is sensitive to any low frequency variation in the DC and provides an amplified output thereof. This signal is passed through a low pass filter circuit comprising resistor 562 in series with resistor 564 which in turn is coupled to the positive input terminal of amplifier 566. The junction 570 between resistor 562 and resistor 564 is coupled via capacitor 568 to the output of amplifier 566. The junction 563 between resistor 564 and the amplifier 566 is coupled to line 548 via capacitor 572. The output of amplifier 566 is also coupled to line 548 via resistor 574 in series with resistor 576. The junction 580 between resistor 574 and 576 is coupled to the negative input terminal of amplifier 566. The output of amplifier 566 on line 581 is the respiration signal.

FIG. 5 further comprises a "trace recover" circuit designated generally 582 coupled to the analog switch which temporarily decreases the high-pass time constant. This circuit is controlled by the system microprocessor. It is activated when the A.C. coupled amp output has saturated, and serves to quickly return the output to the bias point. FIG. 5 also includes a lead fail indicator circuit designated generally 584 coupled to the output of amplifier 524 which detects when no output is present from amplifier 524. Circuits like circuitry 582 and 584 are well known in the art and form no part of the present invention.

Figure 6:
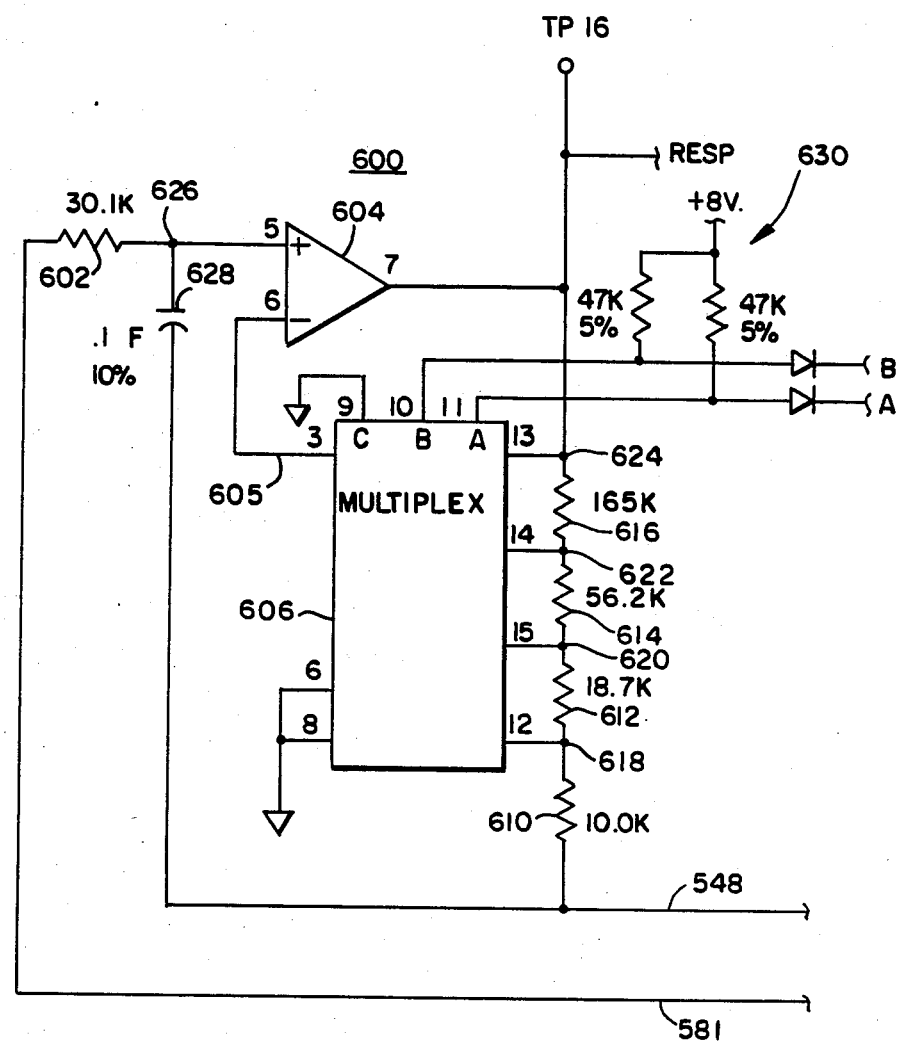
FIG. 6 is a more detailed circuit schematic of a fourth portion of the block diagram of FIG. 2.

Referring now to FIG. 6, a size control or variable gain stage circuit designated generally 600 is disclosed. The respiration signal on line 581 is provided via resistor 602 to the positive input of amplifier 604. The negative input terminal of amplifier 604 is coupled via line 605 to the output of multiplexer circuit 606, an RCA made model no. CD4051B device. The 2.5 volt source on line 548 is connected to the bottom of the divider string formed by the four resistors even numbers 610 through 616 connected in series. The junctions formed by the series resistors, even numbers 618 through 624 are coupled as inputs to the multiplexer. (Line 548 is coupled via junction 626 between the resistor 602 and amplifier 604 via capacitor 628.) Depending on which input is selected for coupling to amplifier 604 by the input selector circuit 630, the gain of amplifier 604 will be greater or lesser and so will be the strength of the respiration signal at its output. The respiration signal can then be digitized and processed by software.

As mentioned earlier a tri-state phase comparator is used in the PLL circuits 330 and 504 so that the PLL VCO runs in phase with the input signal. Tri-state phase comparators have one problem though and that is a dead zone or cross over region which causes noise producing phase jitter when the phase of the incoming signal and the reference are equal, i.e., the comparator will alternate between small positive and negative output signals constantly adjusting the frequency of the VCO. To eliminate this a dead zone circuit is combined with a loop gain circuit and is coupled to the PLL circuits 330 and 504 between pins 9 and 13. The circuits are designated generally 370 in FIG. 3 and 586 in FIG. 5.

The design of circuits 370 and 586 are identical with only the component values being different. Hence, the circuit 586 will be discussed in detail. It comprises a loop filter including the resistor 588 coupled between pins 13 and 9 of the PLL circuit 504, i.e., between the output of the tri-state phase comparator and the input to the VCO. The junction 589 between resistor 588 and pin 9 is coupled to ground through resistor 590 in series with capacitor 591.

The dead zone compensatory portion of the circuit 586 comprises a −5 volt source 592 coupled to the PLL circuit 504 between the resistor 588 and pin 13, the output of the tri-state phase comparator. The −5 volt source is coupled through resistor 593 and parallel capacitor 594. The −5 volt source and resistor allow a small current to trickle out of the phase comparator biasing the output into the positive direction when locked. This eliminates any phase jitter due to the null state of the comparator by preventing operation in this region.

What is claimed is:

1. An apparatus for monitoring the expansion and contraction of the thoracic cavity of a patient during respiration comprising:
   means for generating and coupling to the patient a current carrier signal to be passed through the thorax of the patient;
   means coupled to said carrier generating means for synchronously detecting an amplitude modulated voltage signal developed across the patient in response to the current carrier signal and the patient's varying thoracic impedance due to respiration; and
   means for generating a reference signal for said synchronous detecting means which is in phase with the amplitude modulated voltage signal.

2. The apparatus of claim 1 wherein said reference generating means comprises a phase lock loop circuit which provides a demodulation signal to said synchronous detecting means in response to said amplitude modulated voltage signal.

3. The apparatus of claim 2 wherein said phase locked loop circuit comprises a tri-state phase comparator having a null state and a voltage controlled oscillator (VCO), said tri-state phase comparator having a first input terminal coupled to said amplitude modulated voltage signal and its output terminal coupled to the input terminal of said VCO, said VCO having its output coupled to said synchronous detecting means and a second input terminal of said tri-state phase comparator, said phase locked loop circuit further comprising a dead zone compensation circuit coupled to the input terminal of said VCO to provide a trickle current to said VCO to bias said tri-state phase comparator out of its null state into a predetermined one of its remaining two states.

4. The apparatus of claim 3 wherin said dead zone compensation circuit comprises a voltage source coupled through a circuit including a resistor to said VCO.

5. The apparatus of claim 1 wherin said carrier generating means comprises:
means for generating complementary constant current carriers coupled to the patient through a pair of ECG cables; and
wherein said synchronous detecting means further comprises:
an AC coupled differential amplifier circuit coupled to said carrier generating means and producing an amplified amplitude modulated voltage signal;
a synchronous full wave rectifier circuit coupled to said AC coupled differential amplifier circuit for full wave rectification of said amplitude modulated voltage signal; and
wherein said reference generating means comprises means for generating a pair of complementary reference signals for said synchronous full wave rectification circuit in pahse with said amplified amplitude modulated voltage signal.

6. The apparatus of claim 5 wherein said reference generating means comprises : a phase locked loop circuit having a phase comparator having one input coupled to said amplified amplitude modulation voltage signal a voltage controlled oscillator circuit (VCO) having a frequency twice that of said amplified amplitude modulated voltage signal, said VCO having an input coupled to the output of said phase comparator; said phase locked loop circuit further comprising a flip flop coupled between the output of said VCO, a second input of said comparator and said full wave synchronous detecting means for providing said complementary reference signals thereto and a feedback signal to said phase comparator.

7. The apparatus of claim 6 wherein said phase comparator comprises a tri-state phase comparator having a null phase, said phase locked loop circuit further comprising a dead zone compensation circuit coupled to the input terminal of said VCO to provide a trickle current to said VCO to bias said tri-state phase comparator out of its null state into a predetermined one of its remaining two states.

8. The apparatus of claim 7 wherein said apparatus further comprises an amplifier means AC coupled to the output of said synchronous full wave rectification circuit for providing an amplified respiration signal therefrom.

9. A method for producing a respiration signal representative of the expansion and contraction of the thoracic cavity of a patient comprising the steps of:
coupling a constant current carrier signal to said patient; and
synchronously demodulating an amplitude modulated voltage signal resulting from coupling the constant current carrier signal to said patient using a reference demodulating signal in phase with one derived from said amplitude modulated voltage signal.

10. The method of claim 9 wherein said method further comprises the step of:
generating a pair of complementary constant current carrier signals; and
said coupling step further comprises:
coupling said pair of signals to said patient through a pair of ECG electrodes coupled to said patient.

11. The method of claim 10 wherein said method further comprises the step of:
differentially amplifying the amplitude modulated voltage signals produced by coupling said carrier signals to said patient to produce an amplified AC amplitude modulated voltage signal; and
said demodulating step further comprises:
generating complementary reference signals in phase with and derived from said voltage signal; and
synchronously rectifying said voltage signal in response to said complementary reference signals.

* * * * *

UNITED STATES PATENT AND TRADEMARK OFFICE
CERTIFICATE OF CORRECTION

PATENT NO. : 4,708,146

DATED : November 24, 1987

INVENTOR(S) : Phillip S. Lane

It is certified that error appears in the above—identified patent and that said Letters Patent is hereby corrected as shown below:

Claim 4, line 1, delete "wherin" and substitute therefor --wherein--.

Claim 5, line 1, delete "wherin" and substitute therefor --wherein--.

Claim 5, line 18 delete "pahse" and substitute therefor --phase--.

Signed and Sealed this

Tenth Day of May, 1988

Attest:

DONALD J. QUIGG

*Attesting Officer*      Commissioner of Patents and Trademarks